United States Patent [19]

te Nijenhuis

[11] 4,002,572
[45] Jan. 11, 1977

[54] ALKALINE PROTEASE PRODUCED BY A BACILLUS

[75] Inventor: Bauke te Nijenhuis, Rijswijk-ZH, Netherlands

[73] Assignee: Gist-Brocades N.V., Delft, Netherlands

[22] Filed: Nov. 18, 1975

[21] Appl. No.: 633,026

[30] Foreign Application Priority Data
Nov. 19, 1974 United Kingdom .............. 50044/74

[52] U.S. Cl. .................................. 252/99; 195/62; 195/66 R; 252/DIG. 12; 8/137; 252/89 R
[51] Int. Cl.² .................... C12D 13/10; C11D 7/42
[58] Field of Search ............. 195/62, 65, 66 R, 68, 195/DIG. 11, 2; 252/99, DIG. 12

[56] References Cited
UNITED STATES PATENTS

| | | | |
|---|---|---|---|
| 3,622,458 | 11/1971 | Murao ................................ | 195/62 |
| 3,652,399 | 3/1972 | Isono et al. ........................... | 195/62 |
| 3,674,643 | 7/1972 | Aunstrup et al. .................... | 195/62 |
| 3,684,658 | 8/1972 | Delin et al. .......................... | 195/62 |
| 3,723,250 | 3/1973 | Aunstrup et al. .................... | 195/62 |
| 3,827,938 | 8/1974 | Aunstrup et al. .................... | 195/62 |
| 3,838,009 | 9/1974 | Fukumoto et al. .................. | 195/65 |

*Primary Examiner*—Lionel M. Shapiro
*Attorney, Agent, or Firm*—Hammond & Littell

[57] ABSTRACT

A novel enzyme having a high proteolytic activity in alkaline media and being suitable for inclusion in washing compositions and which is produced by a novel Bacillus strain designated "PB 92", or its proteolytic enzyme producing mutants or variants. A culture of the Bacillus is deposited with the Laboratory for Microbiology of the Technical University of Delft, The Netherlands, where it has been given number OR-60.

7 Claims, 1 Drawing Figure

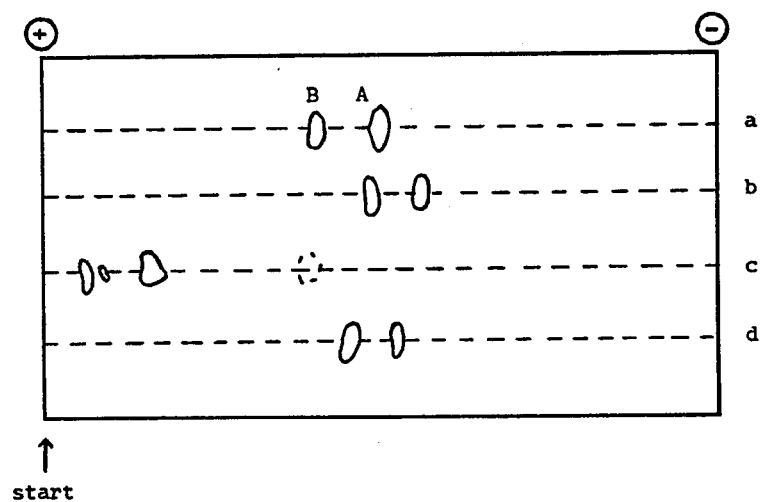

ALKALINE PROTEASE PRODUCED BY A BACILLUS

STATE OF THE ART

Proteolytic enzymes having a high proteolytic activity in the alkaline region are known. Vedder has described in Antonie van Leeuwenhoek, Vol. 1 (1934), p. 141–147, a new microorganism which he called Bacillus alcalophilus, which was able to digest gelatin and haemoglobin in a highly alkaline medium. This property of the microorganism may be ascribed to an enzyme, as later investigations have proved (cf. British patent No. 1,205,403). Enzymes with a high activity in alkaline media are also described in several other references such as British patent No. 1,243,784 and Dutch patent Application No. 72.07050 which disclose several proteolytic enzymes produced by members of the genus Bacillus which are useful in washing compositions normally alkaline when dissolved in the laundry liquid.

OBJECTS OF THE INVENTION

It is an object of the invention to provide a novel proteolytic enzyme having a high activity in the alkaline region.

It is another object of the invention to provide a novel process for the preparation of said novel proteolytic enzyme.

It is a further object of the invention to provide novel washing compositions containing a proteolytic enzyme.

It is an additional object of the invention to provide novel detergents containing a proteolytic enzyme and to a novel method of washing textiles.

These and other objects and advantages of the invention will become obvious from the following detailed description.

THE INVENTION

The novel enzyme of the invention having a high proteolytic activity in alkaline media making it extremely suitable for inclusion in washing compositions, is produced in surprisingly high yields by a Bacillus nov. spec. designated PB 92, or its proteolytic enzyme producing mutants or variants. The yields are higher than those obtained with, for example, a *Bacillus firmus* strain described in Dutch patent Application No. 72.07050. Another unexpected advantage according to the invention is that the enzyme shows a surprisingly good washing action in perborate-containing washing compositions. A culture of the Bacillus PB 92 strain has been deposited with the Laboratory for Microbiology of the Technical University at Delft, the Netherlands and has been assigned the number OR-60.

The novel proteolytic enzyme is produced, according to a feature of the invention, by cultivating Bacillus PB 92 in a nutrient medium containing the usual carbon, nitrogen and trace element sources under aerobic circumstances and isolating the proteolytic enzyme formed from the fermentation broth.

Properties of the enzyme a. pH/activity Relationship

For the determination of the pH/activity relationship, the Anson haemoglobin method was followed [J. Gen. Physiology, Vol. 22 (1939), p. 79–89] as closely as possible. Specifications not given in the Anson literature are indicated hereinafter:

Substrate preparation: Bovin haemoglobin, protease substrate according to Anson, lyophil pure obtained from SERVA, Heidelberg, Germany.

Substrate solution: SERVA haemoglobin was mixed with water by stirring to give a 22% solution (w/v). From this freshly made up concentrated solution, a diluted solution was made containing 8 ml of 1N NaOH, 72 ml of water, 36 g of urea and 10 ml of the concentrated solution. This alkaline solution was kept for 60 minutes at 25° C to denature the haemoglobin. Buffer solutions (see below), urea and merthiolate were added and the pH was adjusted using an Ingold HA electrode, and the volume was adjusted to a haemoglobin concentration of 2.2%. pH reference solutions were obtained from Merck, Darmstadt, Germany (Buffer-Titrisol 8.00, 9.00, 10.00, 11.00 and 12.00). A PHILIPS digital pH meter (PW 9408) was used. For the buffer composition of the pH 8 substrate solution, the description for trypsin determination was followed. The compositions of the other buffer solutions were taken from Dawson et al, ["Data for Biochemical Research", 2nd Ed. (1969) Oxford, pages 475 et seq.]. Components were added to the substrate solution until the final concentrations as indicated below were obtained:

pH range 8.3 – 10.3: glycine - NaOH 0.05 M
pH range 10.8 – 11.3: $Na_2HPO_4$ - NaOH 0.025 M
pH range 11.7 – 12.5: KCl - NaOH 0.05 M Enzyme solution: Solutions were freshly made up in water and a dilution was made, the concentration thereof being 200 DU/ml. The designation of DU means Delft Units, referring to a method for the determination of enzyme activity described in British Patent No. 1,353,317.

Incubation: Each analysis consisted of two determinations and one blank. Substrate and enzyme solutions were placed in a water bath of 25° C and the pH of the substrate solutions was determined by means of an Ingold HA electrode and also by means of an Ingold LOT electrode for pH values below 11.0. Titrisol pH reference solutions were used throughout. 0.5 ml of an enzyme solution were added to 2.5 ml of substrate solution placed in a centrifuge tube and adequate mixing was ensured by stirring immediately with a glass rod provided with a knob. The blank, without the enzyme, was also incubated.

The incubation was terminated after 10 minutes by addition of 5 ml of 0.3N trichloroacetic acid and the blank received 5 ml of the trichloroacetic acid solution and 0.5 ml of enzyme solution. The trichloroacetic acid solution was added by means of a zippette (Jencons, Hemel Hempstead, Hertfordshire). The mixture was stirred vigorously with the glass rod with the knob still in the centrifuge tube and the tubes were placed in a water bath at 2° C.

The pH drift during the incubation was observed by measuring the pH at the beginning and the end of the incubation using a LOT electrode for incubation pH values below 11.0 and a HA electrode for pH values above 11.0. The pH drift was less than 0.1 pH unit for incubations of enzyme solutions containing 50 or less DU/ml and less than 0.15 pH unit for incubations of enzyme solutions containing 200 or 500 DU/ml. Mean values were taken with the Ingold HA values as the basis.

Centrifugation: After at least 30 minutes being kept at 2° C, the tubes were centrifuged at an acceleration of 6,000g.

Color development: The color development was carried out in a water bath at 25° C and 5 ml of supernatant were added to 10 ml of 0.5N NaOH, and the mixture was stirred immediately. After exactly 2 minutes, 3 ml of phenol reagent were added to the mixture with a zippette and with continuous agitation. The phenol reagent was Merck's Folin-Ciocalteus Phenolreagenz, diluted with 2 volumes of water.

The color was read with a spectrophotometer with slit automation at 75 nm exactly 6 minutes after the Folin addition. As a reference for color development, a tyrosin solution contaning $8 \times 10^{-7}$ equivalents of tyrosin in 5 ml of 0.2N HCl with 0.5% (v/v) of formaldehyde was used. The reference color development was checked at regular intervals, but deviations from the mean never exceeded 1% for a batch of diluted Folin reagent.

The enzyme exhibits proteolytic activity as follows:

| pH | 8.3 | 8.8 | 9.4 | 9.8 | 10.3 | 10.8 | 11.3 | 11.7 | 12.5 |
|---|---|---|---|---|---|---|---|---|---|
| relative activity | 85 | 87 | 91 | 88 | 87 | 94 | 91 | 99 | 100 | b. Electrophoresis pattern

The behavior of the enzyme may further be characterized by the zymogram method based on a combination of disc electroporesis in polyacrylamide gel and visual observation of the activity. The method has been described by Zuidweg et al. [Biotech. and Bioeng. Vol. 14, (1972), p. 685–714] and permits a direct comparison of preparations. A comparison has been made of the enzyme of the invention (a), a protease obtained from a Bacillus strain deposited with the National Collection of Type Cultures in London under NCTC 4553, cf British Patent No. 1,205,403 (b), a commercially available proteolytic enzyme Maxatase (Gist-Brocades N.V., Delft, The Netherlands) (c), and a commercially available enzyme Esperase (d), cf the figure of the accompanying drawing. The main components only are indicated. The buffer system used in the electrophoretic separation was system E, containing Tris (i.e. 2-amino-2-hydroxymethyl-1,3-propanediol) and boric acid, and the visual observation of the activity was accomplished by the immersion-contact technique as described in the Zuidweg et al article.

The figure shows that the enzyme of the invention consists of several compounds, the composition of which is different from the compositions of the other enzyme preparations.

c. Amino acid composition

The amino acid composition of the two main components A and B (cf. the attached drawing) was determined. The composition is shown in the table in comparison with the amino acid compositions of several known enzymes: (1) subtilisin Carlsberg, cf. Delange and Smith, J. Biol. Chem. Vol. 243 (1968) p. 2134; (2) the enzyme from Bacillus sacchariticus, cf. U.S. Pat. No. 3,622,458; (3) the enzyme from Bacillus firmus, cf. Dutch Patent Application No. 72.07050, and (4) the enzyme from B 221, cf. K. Horikoshi, Agr. Biol. Chem. Vol. 35 (1971) p. 1407.

The determinations should be considered to be liable to the usual error of ± 10% of the values indicated.

The table further shows the molecular weights of the enzymes, as well as their isoelectronic points.

| Amino acid | (1) | (2) | (3) | (4) | Enzyme of the invention Comp.(A) | Comp.(B) |
|---|---|---|---|---|---|---|
| LYS | 9 | 6 | 4 | 6 | 6 | 6 |
| HIS | 5 | 5 | 6 | 8 | 7 | 6 |
| ARG | 4 | 3 | 6 | 8 | 9 | 8 |
| ASP | 28 | 20 | 23 | 29 | 27 | 28 |
| THR | 19 | 14 | 14 | 18 | 16 | 16 |
| SER | 32 | 37 | 22 | 23 | 30 | 30 |
| GLU | 12 | 12 | 14 | 16 | 15 | 15 |
| PRO | 9 | 10 | 12 | 16 | 12 | 13 |
| GLY | 36 | 25 | 30 | 39 | 31 | 33 |
| ALA | 42 | 27 | 32 | 45 | 36 | 36 |
| CYS | 0 | 0 | 0 | 0 | 0 | 0 |
| VAL | 31 | 20 | 21 | 27 | 22 | 22 |
| MET | 5 | 3 | 2 | 4 | 3 | 3 |
| ILEU | 10 | 12 | 7 | 9 | 8 | 9 |
| LEU | 16 | 12 | 16 | 22 | 18 | 18 |
| TYR | 13 | 9 | 6 | 7 | 7 | 6 |
| PHE | 4 | 2 | 2 | 2 | 2 | 2 |
| TRY | 1 | 3 | — | 5 | 3 | 3 |
| Mol. weight | 27,300 | 22,700 | 26,000 | 30,000 | 25,500 | 25,500 |
| Isoelectric point | 9.3 | 9.3 | 11.0 | 9.4 | 10.5 | 10.5 |

Taxonomy

For the taxonomic determination, use has been made of Smith et al ["Aerobic Sporeforming Bacteria", U.S. Dept. of Agr., Monograph No. 16 (1952)] and sporulation of Bacillus PB 92 was induced by cultivating lyophilized cultures of old TSB (Tryptone Soya Broth, from Oxoid) agar cultures (65 days) on TSB agar.

Morphology a. Vegetative cells: (motile) rods, ends rounded, singular in general, but also in short chains of two to eight rods. Sometimes, very long chains occur having a length of 1000 $\mu$ or more.

b. Sporangia: Sometimes a little swollen.

c. Spores: 0.6 – 0.8 by 1.0 – 1.3 $\mu$; ellipsoidal; thick-walled; subterminal to paracentral.

d. Shadow forms: Rather many; also in the middle of a chain of normal cells.

Further characteristics

Maximum temperature of growth: 50° C.

Gram-positive; obligate aerobic.

Growth on nutrient agar with a pH of 7.2: start somewhat slower than at pH 9.4. Edges of the colonies at pH 7.2 entire, but at pH of 9.4 curled to filamentous.

No formation of a pigment on tyrosine agar at pH of 9.5. Weak starch hydrolysis on potato starch/nutrient agar at pH of 9.5.

Strong liquefaction of gelatin on gelatin/nutrient agar at pH of 9.5. Clear casein digestion on milk agar at pH of 8.4. No or no substantial growth on glucose or mannitol agar with nitrate as the sole nitrogen source. Nitrate reduction positive in nitrate/nutrient broth pH of 9.5.

Isolation

The microorganism producing the enzyme of the invention was isolated from an earth sample from Zambia by means of a specific isolation procedure at a pH within the range of 8.0 to 9.5.

Fermentation

The enzyme produced by the Bacillus PB 92 was obtained by culturing the Bacillus and recovering the enzyme produced in the usual manner. To obtain high yields of the enzyme, media containing well-assimilable carbon and energy sources are necessary such as glucose, sucrose, dextrins and starch, and a nitrogen source of organic origin such as casein, yeast and soya flour. Furthermore, certain amounts of calcium and magnesium salts and several trace elements are preferably added.

A good aeration is necessary during the fermentation and the pH of the medium is suitably kept between 6.5 and 10, preferably between 7 and 9. The fermentation temperature is suitably 37° C. When all these precautions are taken into account, very high yields of protease activity per g of glucose consumed can be obtained. The yield is sufficiently high for an economical production of the enzyme.

Recovery of the enzyme

The enzyme is recovered from the fermentation broth in the usual way. The broth is filtered to remove the microorganisms and insoluble material. For dry washing compositions the enzyme can be precipitated by adding water-miscible organic solvents or inorganic salts such as $Na_2SO_4$ or $(NH_4)_2SO_4$ to the filtrate. For an economical production, the volume of the filtrate is reduced by evaporation first before adding the solvents or salts. For liquid washing compositions the filtered broth or the redissolved enzyme may be used. After precipitation the enzyme is separated by filtration or centrifugation and the resulting cake is dried.

The enzyme may be formulated into washing compositions in the usual manner and washing compositions containing the enzyme form another aspect of the invention. The amount of enzyme to be introduced corresponds generally to that giving the final washing composition a proteolytic activity of about 100 to 5000 DU/g, preferably 500 to 1000 DU/g. The determination of the proteolytic activity is described in British patent No. 1,353,317.

The washing compositions containing the enzyme of the invention further contain at least a detergent. Detergents useful in the washing compositions are those commonly used in washing compositions having enzymatic activity. Generally, non-ionic and anionic surface-active compounds may be used such as water-soluble soaps, anionic, non-ionic, ampholytic and zwitterionic detergents. An example of a commonly used detergent is dodecyl benzene sulfonate. Usually, the detergents, which may be used alone or in an admixture, are present in amounts of about 4 to 20% of the washing composition.

The washing compositions of the invention may contain additional compounds, which are commonly used in other washing compositions having proteolytic activity. They usually contain complex phosphates such as an alkali metal tripolyphosphate or an alkali metal pyrophosphate, preferably in amounts of about 40 to 50% by weight of the washing composition. Furthermore, or alternatively, compounds such as alkali metal cyano-triacetate and alkali metal citrate may be included. Their action in washing compositions is complex, but their most important action is that of water softeners. Other compounds which are usually incorporated are, for example, an alkali metal silicate, usually in amounts of 1 to 10% by weight, weakly alkaline compounds such as an alkali metal bicarbonate, usually in aounts of up to 20% by weight, fillers such as an alkali metal sulfate, and other compounds such as carboxymethylcellulose, perfumes and optical brighteners. Another usually incorporated compound is an alkali metal perborate, especially sodium perborate, and in connection with perborates, it is to be noted that the enzyme according to the invention has an unexpected high stability in the presence thereof.

The washing compositions may be prepared in the usual manner, such as by mixing together the components, or by making first a pre-mix, which is then mixed with the other compounds. Preferably, the enzyme is mixed with one or more of the other compounds, e.g. the filler, to make a concentrate of a predetermined enzymatic activity which concentrate can be mixed with the other desired components.

In the following examples there are described several preferred embodiments to illustrate the invention. However, it should be understood that the invention is not intended to be limited to the specific embodiments.

EXAMPLE 1

The fermentation of Bacillus PB 92 was effected in a medium containing 22 g/liter of yeast (based on dry matter), 5 g/liter of $K_2HPO_4.3H_2O$, 0.05 g/liter of $MgSO_4. 7H_2O$, 0.05 g/liter of $CaCl_2$, 0.005 g/liter of $FeSO_4.7H_2O$ and 0.005 g/liter of $MnSO_4.4H_2O$ and the medium components were dissolved in 90% of the final volume and sterilized at pH 7.0 at a temperature of 120° C for 1 hour. The inoculation culture was obtained by inoculation with Bacillus PB 92 of 100 ml of Trypticase Soya Broth (Oxoid), to which after sterilization for 20 minutes at 120° C, 4 ml of 1M sodium carbonate solution was added from a slant tube. The inoculation culture was incubated at 30° C for 24 hours on a shaking apparatus.

The medium was inoculated at 37° C and a pH of 8.0 with 1 volume of the inoculation culture per 100 volumes of medium. The main fermentation was carried out at 37° C in stirred fermenters equipped with a pH controlling device, a temperature controlling device, an antifoaming device and a device for continuous measurement of the dissolved oxygen concentration and the oxygen uptake rate. 17 hours after inoculation, a 30% glucose solution sterilized at 120° C for 1 hour was added to a final concentration of 30 grams of glucose per liter of medium. The results obtained indicate a yield of the novel proteolytic enzyme of about $8 \times 10^5$ DU per gram of glucose consumed.

In Example 1 of Dutch Patent Application Ser. No. 72.07050, a fermentation experiment is described in which a final yield of $11 \times 10^6$ DU/liter of broth is obtained (50 Anson Units equals approximately $11 \times 10^6$ DU). The quantity of carbohydrate employed is equivalent to approximately 75 grams of glucose per liter of broth and the yield of protease per g of glucose consumed in Example 1 of Application No. 72.07050 amounts to $1.5 \times 10^5$ DU. Thus, the yield of the invention is about 5 times higher.

EXAMPLE 2

Washing action

Washing tests were carried out in the following manner with test pieces of cloth: EMPA-116 (stained with blood, milk and chinese ink) obtained from Eidgenössische Material Prüfungs - und Versuchsanstalt für Industrie, Bauwesen und Gewerbe at Skt. Gallen, Switzerland). The test pieces were stored in air-tight darkness. For a washing test, the necessary pieces of 5 × 5 cm were cut from a visually homogeneous part of the cloth.

Laundry suds: 4 g/liter of a perborate-containing commercially available washing agent with enzymes omitted per liter of "synthetic tap water" (STW) having a German Hardness of 15° DH, prepared as follows: 10 ml of a 2% $CaCl_2$ (pro analysis) solution in distilled water were added to 10 ml of a solution of 0.656% of $MgCl_2$ in distilled water in a 1000 ml volumetric flask. The contents were mixed thoroughly and then, 10 ml of a 2.1% $NaHCO_3$ (pro analysis) solution were added. The contents were mixed again, and filled up with distilled water to make the 1000 ml.

250 ml of the laundry suds were added into each of a sufficient number of 300 ml Erlenmeyer flasks. Amounts of enzyme corresponding to 0, 250, 500, and 1000 DU/g of washing composition were added in duplicate and the Erlenmeyer flasks were placed in a shaken thermostat kept at 45° C wherein they were allowed to warm up with agitation. Then, a piece of cloth was added to each of the Erlenmeyer flasks which was then shaken for exactly one hour at 45° C.

After the washing, the laundry suds were decanted and 250 ml of STW were added. The vessels were closed with rubber stoppers and were shaken vigorously for exactly one minute. The pieces of cloth were collected in a beaker in which they were rinsed in slowly flowing tap water. After addition of the last piece of cloth, the rinsing was continued for about 10 minutes and then the pieces of cloth were folded in a white clean towel and allowed to dry in air in darkness.

After drying, the remission was estimated in a remission meter with filter No. 1, at both sides, using MgO as a reference. The average values were calculated with reference to an entirely clean-washed piece of cloth having a remission of 65.8% against MgO. Comparison of the enzyme of the invention and Maxatase and Esperase were made and the washing tests were carried out in the above-indicated manner at a pH of 9.7. The results were as follows:

| DU/g | enzyme of invention % remission | Δ % | Maxatase % remission | Δ % | Esperase % remission | Δ % |
|---|---|---|---|---|---|---|
| 0 | 20 | — | — | — | — | — |
| 250 | 41 | 21 | 30 | 10 | 31 | 11 |
| 500 | 46 | 26 | 33 | 13 | 36 | 16 |
| 1000 | 52 | 32 | 36 | 16 | 39 | 19 |

The table shows that, under the test conditions the enzyme of the invention has a better washing action than the commercially available Maxatase and Esperase.

Various modifications of the compositions and processes of the invention may be made without departing from the spirit or scope thereof and it should be understood that the invention is intended to be limited only as defined in the appended claims.

I claim:

1. A process for the preparation of an enzyme having high proteolytic activity in alkaline media comprising cultivating Bacillus strain PB 92 in a nutrient medium and recovering the formed proteolytic enzyme.

2. The process of claim 1 wherein the nutrient media contains carbon, nitrogen, calcium salts, magnesium salts and trace elements under aerobic conditions.

3. The process of claim 1 wherein the fermentation broth is filtered, the enzyme is precipitated from the filtrate, recovering and drying the precipitate to recover the enzyme.

4. An alkaline protease produced by cultivation of Bacillus nov. sp. PB 92 and characterized by the following properties:

a optimal proteolytic activity at a pH value above 12, said activity being measured against denatured hemoglobin according to the Anson method, b. consisting of at least three proteolytically active components showing a characteristic zymogram following disc electrophoresis as shown in the accompanying figure, c) the two main components having the following amino acid composition:

| | component 1 | component 2 |
|---|---|---|
| Lysine | 6 | 6 |
| Histidine | 7 | 6 |
| Arginine | 9 | 8 |

-continued

| c) the two main components having the following amino acid composition: | | |
|---|---|---|
| Asparctic acid | 27 | 28 |
| Threonine | 16 | 16 |
| Serine | 30 | 30 |
| Glutamic acid | 15 | 15 |
| Proline | 12 | 13 |
| Glycine | 31 | 33 |
| Alanine | 36 | 36 |
| Cystine | 0 | 0 |
| Valine | 22 | 22 |
| Methionine | 3 | 3 |
| Isoleucine | 8 | 9 |
| Leucine | 18 | 18 |
| Tyrosine | 7 | 6 |
| Phenylalanine | 2 | 2 |
| Tryptophan | 3 | 3 |

| d) the two main components having the following physical properties | | |
|---|---|---|
| isolectric point | 10.5 | 10.5 |
| molecular weight | 25,500 | 25,500 | e. showing an improved washing action in perborate containing washing compositions.

5. A washing composition containing an effective amount of the enzyme of claim 4 having a high proteolytic activity in alkaline media.

6. The washing composition of claim 5 also containing a detergent, a water softener, an alkali metal silicate, a weakly alkaline bicarbonate and optionally an alkali metal per borate.

7. A method of cleaning textiles comprising washing textiles in an aqueous solution containing an effective amount of the washing composition of claim 6.

* * * * *